United States Patent [19]

Scholz

[11] Patent Number: 5,820,253
[45] Date of Patent: Oct. 13, 1998

[54] LIGHT FOR MEDICAL USE

[75] Inventor: Manfred Scholz, Seitingen, Germany

[73] Assignee: Delma elektro- und medizinische Apparatebau Gesellschaft mbH, Tuttlingen, Germany

[21] Appl. No.: 707,810

[22] Filed: Aug. 30, 1996

Related U.S. Application Data

[63] Continuation of Ser. No. 335,295, Nov. 7, 1994, abandoned.

[30] Foreign Application Priority Data

Nov. 15, 1993 [DE] Germany .................. 43 38 977.5

[51] Int. Cl.⁶ .................................................. F21V 29/00
[52] U.S. Cl. .................... 362/267; 362/287; 362/804; 362/310; 362/293; 362/419; 362/373
[58] Field of Search ................................. 362/804, 419, 362/287, 285, 294, 373, 310, 418, 371, 370, 374, 375, 284, 223, 298, 300, 302, 303, 319, 271, 277, 267

[56] References Cited

U.S. PATENT DOCUMENTS

| | | |
|---|---|---|
| 2,173,325 | 9/1939 | Alexander . |
| 2,426,436 | 8/1947 | Cochener ............................ 362/371 |
| 3,240,925 | 3/1966 | Paschke et al. .................... 362/275 X |
| 3,348,036 | 10/1967 | Bodian et al. ...................... 362/373 X |
| 4,423,471 | 12/1983 | Gordin et al. ...................... 362/419 X |
| 4,535,395 | 8/1985 | Prester ................................. 362/267 |
| 4,578,742 | 3/1986 | Klein et al. ......................... 362/373 |
| 4,587,601 | 5/1986 | Collins ................................ 362/303 X |
| 4,651,257 | 3/1987 | Gehly .................................. 362/303 X |
| 4,692,848 | 9/1987 | Poyer .................................. 362/267 |
| 4,890,208 | 12/1989 | Izenour ............................... 362/294 |
| 4,930,058 | 5/1990 | Jones . |
| 4,999,758 | 3/1991 | Wimberly ........................... 362/373 |
| 5,038,255 | 8/1991 | Nishihashi . |
| 5,165,786 | 11/1992 | Hubert ................................ 312/804 X |
| 5,321,595 | 6/1994 | Jacobi et al. ....................... 362/264 |
| 5,394,316 | 2/1995 | Holbrook ........................... 362/374 X |
| 5,528,474 | 6/1996 | Roney et al. ....................... 362/294 |

FOREIGN PATENT DOCUMENTS

| | | |
|---|---|---|
| 0 140 390 | 5/1985 | European Pat. Off. . |
| 2 390 670 | 12/1978 | France . |
| 2 403 515 | 4/1979 | France . |
| 869671 | 1/1953 | Germany . |
| 1 036 787 | 11/1961 | Germany . |
| 6752421 | 3/1969 | Germany . |
| 25 35 556 | 2/1976 | Germany . |
| 78 28 107 | 3/1980 | Germany . |
| 8115935 U | 9/1981 | Germany . |
| 32 22 501 | 12/1982 | Germany . |
| 33 39 789 | 9/1985 | Germany . |
| 8309857 U | 11/1986 | Germany . |
| 8630408 U | 2/1987 | Germany . |
| 34 37 626 | 9/1987 | Germany . |
| 36 22 109 | 1/1988 | Germany . |
| 38 17 131 | 11/1989 | Germany . |
| 38 37 833 | 5/1990 | Germany . |
| 8903957 U | 11/1990 | Germany . |
| 9017143 U | 4/1991 | Germany . |
| 9204644 U | 11/1992 | Germany . |

OTHER PUBLICATIONS

"Hygiene und Design: Neues OP–Leuchtenkonzept für pflegeleichte Funktionalität", in: Krankenhaus Technik, Jun. 1990, pp. 46–48.

Saechtling, Hansjürgen, *Kunstoff–Taschenbuch*, 21st ed., Carl Hanser Verlag, Munich, Vienna, 1979, pp. 466–467.

*Primary Examiner*—Thomas M. Sember
*Attorney, Agent, or Firm*—Townsend and Townsend and Crew LLP

[57] ABSTRACT

A light for medical purposes has a lamp housing (11), at least one lamp (12) arranged therein, a reflector (16) arranged therein, and a light transmissive plate arrangement (13) closing off the lamp housing (11) towards the illumination field (14). The lamp housing (11) with the light transmissive plate (13) is closed off towards the exterior for reasons of hygiene and is formed from a material with a lower thermal conductivity than that of human skin, at least at those sites at which a contact by the operating person can arise.

9 Claims, 3 Drawing Sheets

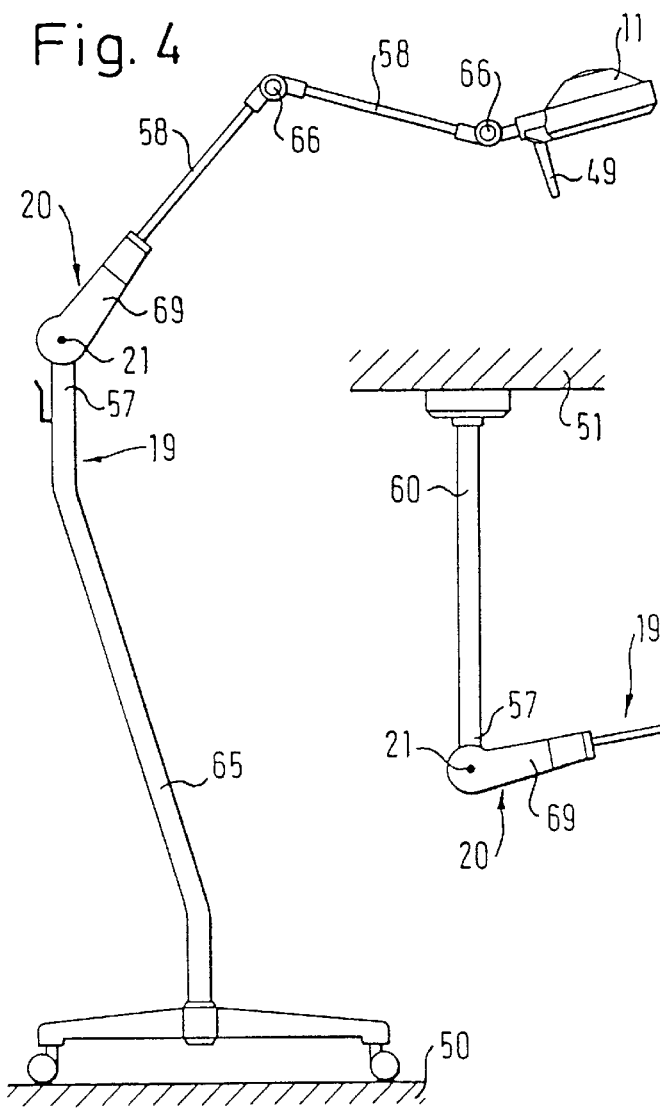
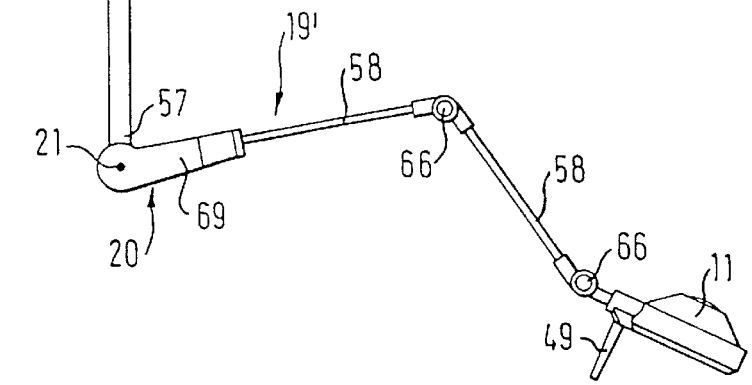
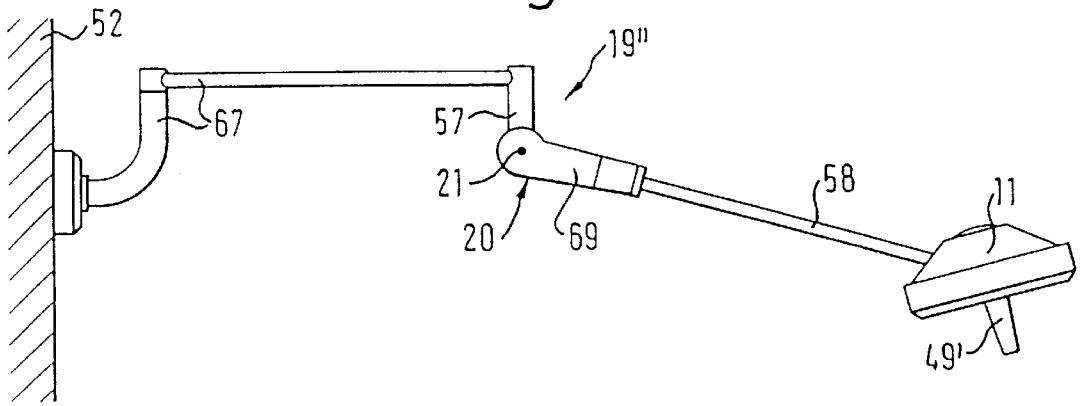

LIGHT FOR MEDICAL USE

This is a continuation of application Ser. No. 08/335,295, filed Nov. 7, 1994, now abandoned.

BACKGROUND OF THE INVENTION

The invention relates to a light for medical use, in particular to a medical examination light with a lamp housing, at least one lamp arranged therein, a reflector arranged in the lamp housing and surrounding the lamp, and a light transmissive plate arrangement closing off the lamp housing towards the illumination field.

Known examination lights of this type should exhibit daylight characteristics in their colour temperature and color reproduction. Furthermore, high illuminations are demanded with a minimum of infrared-radiation and ultraviolet-radiation. The light housing should be closed for hygienic reasons. Furthermore, the light housing must be compact and may not cause burns in the user and patients in the case of contact during operation. A cost-favorable manufacture must also be possible.

The light must be robust, stable, and safely built. No lacquer may crack off and no dents may arise through damages. The exchanging of the lamp or the bulb must be able to be carried out easily and simply. The lamp and the reflector should be finely adjustable in order to ensure constant light quality.

Up to now, it has not been possible to simultaneously fulfill these requirements with the known examination lights. Thus, it is for example difficult to obtain high light powers on the one hand, and on the other hand to keep the lamp housing at low exterior temperatures. Therefore, with known operation light housings, cooling slits are often arranged for cooling, which is, however, undesirable for reasons of hygiene. Closed operation lights are also already known in which, however, the light housing becomes very warm, so that the user can burn himself with it.

SUMMARY OF THE INVENTION

The goal of the present invention is to provide a light for medical use of the initially named kind which is absolutely unproblematic with respect to the hygiene, which has a high strength of illumination, and which at the same time can be contacted by the user without danger of being burned.

In order to satisfy these contradicting requirements, there is provided a light of the initially named kind which is characterized in that the lamp housing is closed off towards the exterior in such a manner that there are no cooling air convection openings, in particular no cooling slits provided on it, and is formed from a material with a lower thermal conductivity than that of human skin, at least at those sites at which a contact by the operating person can arise.

The inventive concept is thus to be seen in that a strong heating which results from high light power and from a closed lamp housing is accepted, however, is made harmless by keeping the thermal conductivity of at least those sites which a user is to contact so small that, upon contact by the user, at first so much heat is suddenly dissipated from the surface of the lamp housing or of the light transmissive plate that the temperature there is correspondingly quickly lowered so far that a burn can no longer occur. Since an intensive heat supply to the site of contact is avoided at the same time through the high thermal insulation of the material, the temperature at the contact site can on the whole be kept at a value which lies below the burning limit. In other words, in the case of a contact, the contacted site at the lamp housing or the light transmissive plate is cooled to an acceptable temperature by the skin of the user himself, since the heat supply progresses slower over the heat insulating material than the heat dissipation over the body of the user. Accordingly, the contact temperature is kept substantially lower than the otherwise inherently present surface temperature of the material. These considerations are valid for the light transmissive plate arrangement only if this is also formed with a thermal conductivity in accordance with the invention.

Because of the embodiment in accordance with the invention, the lamp housing or the light transmissive plate may definitely reach a substantial surface temperature of, for example, 70° C., through which an intensive cooling is obtained in an advantageous manner through heat radiation, which ensures a satisfactory dissipation of the heat generated by the high light intensity. Nevertheless, a burn of the user's part of the body which contacts the lamp body or the light transmissive plate is effectively avoided by the local contact cooling.

The thermal conduction coefficient of human skin can be assumed to be 0.5 to 0.6 W/m·°K. With this condition, it is particularly advantageous, if the material has a thermal conduction coefficient of 0.15 to 0.25 W/m·°K. at those sites where it can be contacted by the user. Such a thermal conduction coefficient on the one hand prevents such an intensive heat supply to the contact site that there is a danger of being burned, on the other hand however is still sufficient to dissipate the heat which is generated by the lamp, and the heat of the filters which is caused by absorbed infrared-radiation and ultraviolet-radiation.

An increased temperature in the interior of the light is thus deliberately accepted in accordance with the invention. In this regard, the exterior temperature almost remains unchanged because of the heat transfer conditions. In the case of contact, the skin dissipates more heat than is supplied by the housing material. Therefore the contact temperature sinks considerably.

The embodiments characterized in that the lamp housing has a covering hood which can be pivoted in the upward direction and which covers the reflector from the top and partially also from the side, wherein the covering hood can preferably be pivoted so far in the upward direction that the lamp mount becomes accessible and thus that the lamp can be exchanged while the covering hood is pivoted in the upward direction, and in that a manually actuated lock mechanism is provided for the mounting of the covering hood in the closed position, and in that in the closed position, the covering hood is loaded by a spring force which acts in the opening direction and which lifts the covering hood by a preset small portion during the unlocking of the lock mechanism, such that the covering hood subsequently can comfortably be grasped and opened further, and in which the light in which the lamp housing is secured to the floor, to the ceiling, to the wall of a room or to another object via a linkage is characterised in that a gas spring joint arrangement is put into the linkage in such a manner that the lamp housing is pivotable about the rotation joint of the gas spring joint arrangement and is at least approximately in equilibrium with respect to the rotation joint by at least one gas spring which is arranged in the gas spring joint arrangement, ensure an unproblematic accessibility to the interior of the lamp housing.

A simple pivotal adjustment of the lamp housing is possible as a result of the features of the light, in which the lamp housing is secured to the floor, to the ceiling, to the wall of a room or to another object via a linkage, characterized in that a gas spring joint arrangement is put into the linkage in such a manner that the lamp housing is pivotable about the rotation joint of the gas spring joint arrangement and is at least approximately in equilibrium with respect to the rotation joint by at least one gas spring which is arranged in the gas spring joint arrangement, and in which an arm of the gas spring joint arrangement has a substantially horizontal normal position and is pivotable about this normal position in the upward and downward directions, and in which the angle of pivoting about the horizontal normal position is preferably ±45° and in particular ±60°, and in which the gas spring joint arrangement has a sine characteristic curve such that, independent of its pivotal position, there is always at least substantially an equilibrium between the torques about the rotation joint which are exerted by the lamp housing and the parts attached to it, and the gas spring joint arrangement, and in which a preferably adjustable friction brake is provided in the joint of the gas spring joint arrangement, wherein the brake force is only to be large enough that the lamp housing is still pivotable about the joint with small forces, and that possible imbalance weights which may still remain despite the insertion of the gas spring joint arrangement are absorbed by the friction brake, and in which the lamp mount is releasably attached to the reflector from above, and in which the lamp mount carries the lamp via a carrier rod which is adjustable in the direction of light emission.

Because the lamp mount is releasably attached to the reflector from above, carries the lamp via a carrier rod which is adjustable in the direction of light emission, and because a counter-reflector which is small in relation to the reflector and which is preferably adjustable in the direction of light emission is arranged in front of the lamp, a simple exchanging of the lamp is possible, and the lamp, as well as the counter-reflector, can be adjusted to an optimum.

Advantageous further embodiments of the invention are characterized by the lamp housing comprising plastic, the light transmissive plate arrangement comprising a single light transmitting plate, the light transmissive plate arrangement comprising two light transmitting plates which are preferably parallel to one another and which in particular are arranged with a distance to one another, the light transmissive plate arrangement comprising plastic or glass, one light transmissive plate—preferably the upper one—being an infrared-filter, a light transmissive plate being coated with a foil, and this foil being a conversion foil and/or filter foil.

DESCRIPTION OF THE PREFERRED EMBODIMENTS

Figure 1:
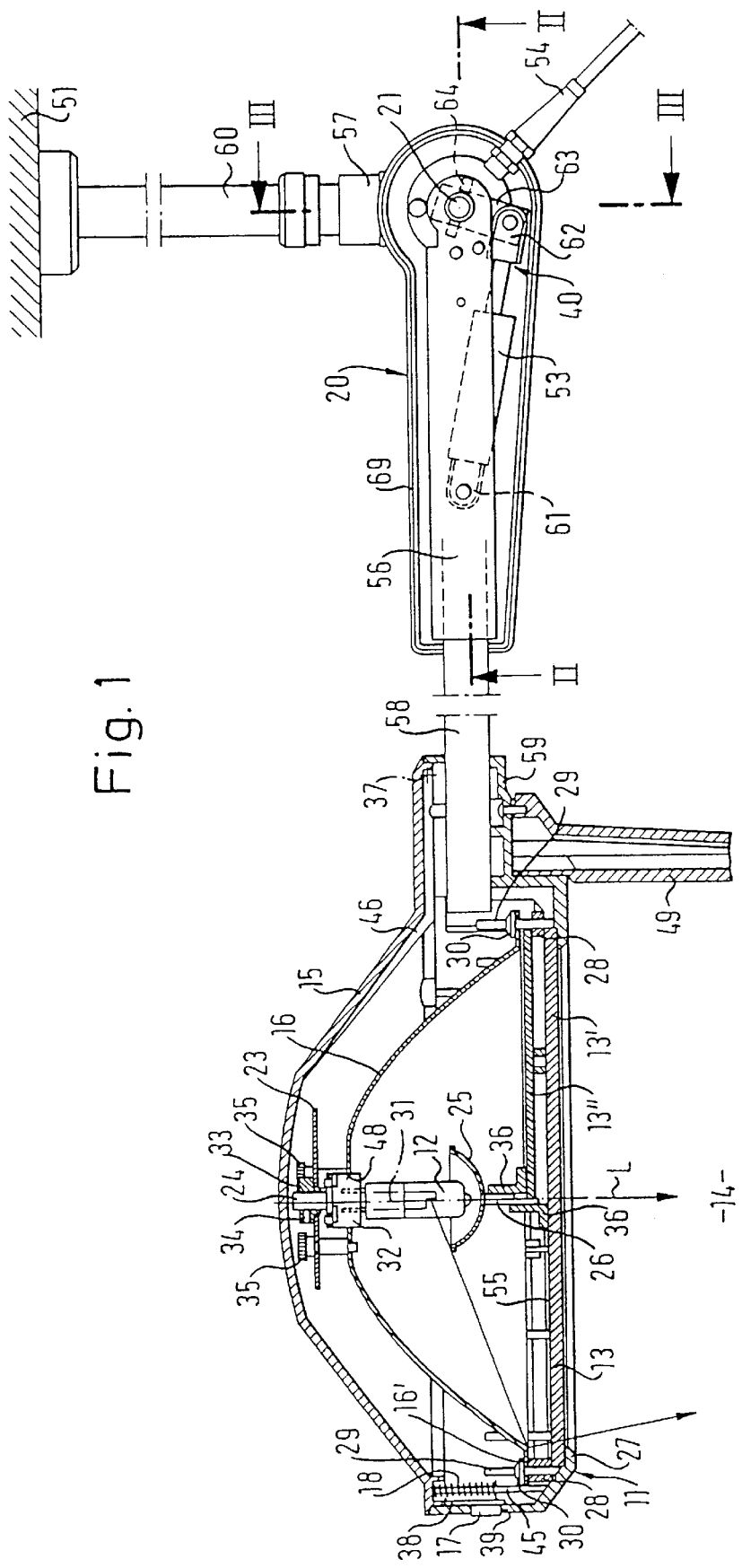
FIG. 1 is a vertical longitudinal section through an operation light made in accordance with the invention.

In accordance with FIG. 1, a lamp housing 11 is arranged on a horizontal pivot arm 58. It exhibits an opening at the bottom, in which a light transmissive plate 13, which is coated with a filter foil 55 can be arranged. Such an arrangement of the light transmissive plate 13 is represented to the left of the center axis 31. Another embodiment, with two light transmissive plates 13', 13" which are arranged on top of one another and of which the top one can have filter characteristics is drawn to the right of the center axis 31. The light transmissive plates 13, 13', 13" can be made from glass or plastic. The edge 16' of a parabolic mirror-like reflector 16 is mounted on distance pieces 28 around the light transmissive plate 13 or 13' which lies on a radial interior ring projection 27, with stud bolts 29, on which spring nuts 30 are pushed, passing through the distance pieces 28 in order to fix the edge 16' at the lamp housing 11.

The reflector 16 has a central opening 48 in the crown, through which the base 32 for a lamp 12 arranged in the interior of the reflector extends. At the top of the base 32, a carrier rod 24 is coaxially secured to the central axis 31 which extends through a liner 33 which is secured to a plate-like lamp mount 23. The carrier rod 24 can be fixed in different positions of height at the lamp mount 23 via a headless screw 34 which is radially screwed in the liner 33.

The lamp mount 23 is releasably secured to the crown of the reflector 16 via knurled screws 35.

A counter-reflector 25 which is arranged to vertically slide in a liner 36 via a carrier rod 26 extending in the downward direction and which is arranged to be adjustable via a non-represented continually resilient screw retention, is under the lamp 12 and is formed substantially smaller in the reverse arrangement as the reflector 16. The liner 36 is secured to the top of the light transmissive plate 13 or 13".

The lamp 12 radiates its light in an illumination field 14 which is under the light transmissive plate 13 or 13', 13" via the reflector 16.

Above the reflector 16, there is a covering hood 15 which is pivotally secured on a side about an axis 37 to a base body 59 in which the one end of the pivot arm 58 is attached. A vertically extending flexible tongue 38, which at the bottom has an unlocking button 17 which radially points to the outside and which resiliently engages in a radial lock bore 39 of the lamp housing 11 through the flexible tongue 38, is arranged at the diametrically opposite side at the bottom at the edge of the covering hood 15 at the interior of the lamp housing 11. An erection spring 18 which under prestress acts from the bottom at the edge of the covering hood 15 and which is supported at the lamp housing 11 vertically extends immediately radially in the interior of the flexible tongue 38.

The other end of the pivot arm 58 is secured in a gas spring joint arrangement 20, which has a substantially horizontal lever arm 56 which is pivotable about a joint 21 in the upward and downward directions, and a substantially vertically arranged fixed lever arm 57 which can, for example, be secured to the ceiling 51 of a room via a rod 60. The pivot arm 58 and the lever arm 56 could also be formed as one piece.

The lever arm 56 is linked to the one end 61 of a gas spring 53 in a clear distance from the joint 21. In accordance with FIG. 1, the gas spring 53 extends from this link point in an inclined manner to the longitudinal axis of the lever arm 56 to the bottom, where its other end 62 is linked to a lever 63, which extends away from the joint 21 approximately perpendicular to the longitudinal extension of the gas spring 53, and which has a bore 73 which is concentric to the joint 21 in accordance with FIGS. 2, 3, and which is non-rotatably connected to the fixed lever arm 57 via a connection shaft 72 which is arranged in the bore 73. In accordance with the invention, the lever 63 can be fixed in different angular positions with respect to the axis of the rotation joint 21 at the lever arm 57. The angularly adjustable attachment of the lever 63 to the lever arm 57 can occur in accordance with the FIGS. 2 and 3 via a placement of pins 64, which permits various angular positions, between the lever 63 and the connection shaft 72 which penetrates its bore 73. The connection shaft 72 extends from the bore 73 to a pocket bore 74, which is aligned with it, of a block 71 to which the second lever arm 57 is secured in the manner apparent from FIGS. 2 and 3, and is also secured there via a transverse placement of pins 75.

Figure 2:
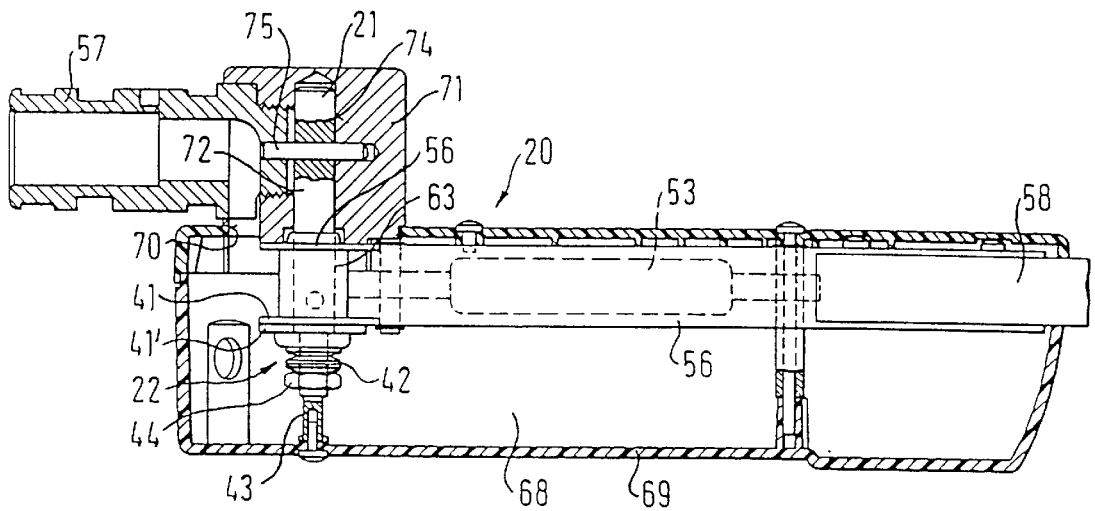
FIG. 2 is a section taken along line II—II in FIG. 1.
Figure 3:
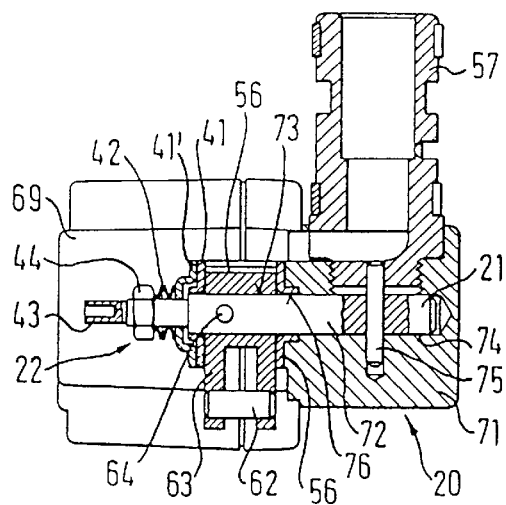
FIG. 3 is a section taken along line III—III in FIG. 1, and FIGS. 4–6 show various arrangements for mounting the lamp housing in accordance with the invention with adjustable rod assemblies on differently oriented surfaces.

In accordance with FIGS. 1 to 3, the lever arm 56 is surrounded by a housing 69 which is preferably made from plastic and which surrounds the face end of the block 71 facing the lever 63 with a lateral opening 70 in a sliding connection. The block 71 is thus arranged in the region of the joint 21 beside the end of the lever arm 56 there which is formed as a U-profile in this region and which is rotatably arranged on the connection shaft 72 via bores 76. The upper limb in FIG. 2 and right limb in FIG. 3 at the end of the lever arm 56 thus lies between the lever 63 and the block 71 in the manner apparent from the FIGS. 2 and 3.

In accordance with FIG. 1, a current connector 54 is provided close to the joint 21 at the housing 69, through which the non-represented electrical leads for the operation of the light can be installed.

The force of the gas spring 53 is selected such that the torque acting in the upward direction on the arm 56 is approximately in equilibrium with the weight of the lamp housing 11 including the construction elements secured to it. For this, the gas spring joint arrangement 20 has a sine characteristic curve in such a manner that the weight torque which changes during the upward and downward pivoting of the lamp housing 11 is compensated in every case by the gas spring 53.

In accordance with FIGS. 2 and 3, a friction brake 22, which comprises brake disks 41, 42' which are rotatably and non-rotatably arranged on the connection shaft 72, disk springs 42, and a hexagon nut 44 screwed to an axle 43, is arranged at the pivot joint 21 between the two lever arms 56, 57, which permits the brake disks 41, 41' to be pressed against one another with a well-defined axial force. The brake disk 41 which is to the right in FIG. 3 is formed at the lower limb in FIG. 2 and at the left limb in FIG. 3 of the U-shaped end of the lever arm 56, thus being non-rotatably connected to the lever arm 56, while the left brake disk 41' is non-rotatably arranged on the connection shaft 72.

This generates a defined static friction and sliding friction, which ensures an exact and comfortable fixing of the gas spring joint arrangement 20 in every desired position. Small imbalance weights between the lamp housing 11 and the construction elements attached to it on the one hand, and the gas spring joint arrangement 20 on the other hand, are also compensated by the friction brake 22.

The lamp housing 11 is provided with vertical supports 45 and the covering hood is provided with ribs 46 in order to increase stiffness.

Further construction elements, for example, the mains supply unit for the lamp 12, can be accommodated in the interior 68 (FIG. 2) of the housing 69 aside from the gas spring 53 itself.

The function of the described operation lamp is as follows:

In order to execute an exchanging of the lamp, the push button 17 is actuated which causes it to disengage from the lock bore 39 and thus permits that the erection spring 18 can pivot the covering hood 15 by a small portion in the upward direction. Now the actuating person can grasp under the exposed edge of the covering hood 15 and completely tilt it in the upward direction and to the right in FIG. 1.

In this state, the knurled screws 35 can be screwed off, which permits that the lamp mount 23 can be removed with the base 32 and the lamp 12 for the exchanging of the lamp. In the reverse manner, the lamp mount 23 is inserted again after exchanging the lamp 12, which permits that a suitable axial adjustment of the lamp 12 can be performed by releasing the headless screw 34 and axially displacing the carrier rod 24. Now, the counter-reflector 13 can also be brought into the optimum adjustment position by vertically adjusting the carrier rod 26 within the liner 36. Instead of securing a smooth carrier rod 26 with a headless screw, the carrier rod 26 can also be formed as a threaded bolt which is arranged in a liner 36 provided with an internal thread. In this case, the height adjustment of the counter-reflector 25 can occur by simply rotating the counter-reflector 25 in the one or the other direction.

In order to adjust the counter-reflector 25, the covering hood 15 is tilted open and the lamp mount 23 with the lamp base 32 and the lamp 12 is removed. The adjustment is then performed through the opening 48 in the crown of the reflector 16. This adjustment already occurs during the manufacturing process and is in general kept later.

After the adjustment of the counter-reflector 25 has been performed, the lamp mount 23 is assembled with the base 32 and the lamp 12, and the lamp 12 is also adjusted by adjusting the carrier rod 24 in the vertical direction.

A handle 49 which is provided at the base body 59 and which projects in the downward direction is gripped during normal use, and the actuating person can now bring the lamp housing 11 into the desired pivot position by upwardly and downwardly moving the handle 49 to the left and to the right. In this case, the gas spring joint arrangement 20 ensures that this pivotal movement can be performed largely without force, while the friction brake 22 ensures that the lamp housing 11 retains the reached position after successful displacement.

In accordance with FIG. 4, the lamp housing 11 fitted with the handle 49 is secured to the lever arm 56 of the gas spring joint arrangement 20 in accordance with the invention via two pivot arms 58 which are connected to one another and to the lamp housing 11 via joints 66. The fixed arm 57 of the gas spring joint arrangement 20 is secured to a stand 65 which is movable on the floor 50 of a room. In this manner, a linkage (rod assembly or arm assembly) 19 is brought about which carries the lamp housing 11 and which can be moved to a desired location of operation. The joints 66 between the lamp housing 11 and the one pivot arm 58 or between the two pivot arms 58 should be fixed during normal use, so that a pivoting of the lamp housing 11 is only possible about the joint 21 of the gas spring joint arrangement 20 in accordance with the invention during the gripping of the handle.

FIG. 5 shows a ceiling attachment for the light in accordance with the invention. For this, a rod 60 extends from the ceiling 51 of a room—as in the embodiment of FIG. 1—in the downward direction to the upright standing second lever arm 57 of the gas spring joint arrangement 20 to which it is fixedly connected. The second lever arm 56 of the gas spring joint arrangement 20 once again extends substantially horizontal and is connected to the lamp housing 11 via two pivot arms 58 and joints 66 which may be locked. The rod 60, the gas spring joint arrangement 20, as well as the pivot arms 58 form a linkage 19' which holds the lamp housing 11 to the ceiling 51 of a room.

FIG. 6 shows a different embodiment in which the lamp housing 11 has a central peg 49' as a handle. In this case, the lamp housing 11 is immediately secured to the pivotable lever arm 56 of the gas spring joint arrangement 20 via a pivot arm 58, with the fixed lever arm 57 of the gas spring joint arrangement 20 being secured to the wall 52 of a room via a rod arrangement 67. In this manner, the lamp housing 11 which easily can be pivoted in the upward and downward directions is secured to the wall 52 of a room via a linkage 19".

What is claimed is:

1. Light for medical use comprising a lamp housing free of cooling slits, made from a material with a lower thermal conductivity than that of human skin, at least where the housing can be contacted by a person using the light, the housing having an opening and at least one lamp arranged in the housing, a reflector arranged in the lamp housing surrounding a portion of the lamp, a light transmissive plate arrangement closing the opening, the lamp housing having a hood covering a side of the reflector facing away from the opening and pivotable in a direction away from the reflector to provide access to and permit exchange of the lamp, a manually actuated lock mechanism for holding the hood in a closed position, a spring acting on the hood, biasing it in said direction and which, on release of the lock mechanism, moves the hood a preset, relatively small portion so that the hood can subsequently be comfortably grasped and opened further.

2. Light for medical use comprising a lamp housing having an opening and at least one lamp arranged therein for directing light through the opening, a linkage for supporting the light, a gas spring joint operatively coupled with the linkage and the lamp housing and permitting the lamp housing to pivot in generally, up and down directions about a normally horizontal pivot axis defined by the gas spring joint, the gas spring joint including at least one gas spring adapted to maintain the lamp housing in an at least approximate equilibrium with respect to the pivot axis when the lamp housing is supported by the linkage, the gas spring joint having a sine characteristic curve such that, independent of its pivotal position, there is always at least substantially an equilibrium between respective torques exerted by the lamp housing and the gas spring joint about the pivot axis, an arm extending from the lamp housing, an intermediate member connecting the arm and the gas spring joint which is movable relative to both, and a handle operatively coupled with the lamp housing and oriented transversely to the arm for manipulating the housing via the arm relative to the pivot axis.

3. A medical examination light for medical use comprising a lamp housing free of vent apertures communicating an interior of the housing with an exterior thereof, having an opening and at least one heat emitting lamp arranged in the housing interior, directing its light through the opening and generating sufficient heat when in use so that the housing is heated to a temperature of at least about 70° C., a reflector arranged in the lamp housing surrounding a portion of the lamp, a light transmissive plate arrangement closing the opening, and infrared filter means arranged in the lamp housing between the lamp and the opening, the lamp housing and the plate defining an enclosure for an interior of the light which is free of openings, the lamp housing being made of a material having a thermal conductivity which is lower than that of human skin so that a user of the light can touch the lamp housing without adverse effects due to the elevated housing temperature and a contamination of the housing interior is prevented.

4. Light for medical use comprising a lamp housing free of vent apertures communicating an interior of the housing with an exterior thereof, having an opening and at least one heat emitting lamp arranged in the housing interior, directing its light through the opening and generating sufficient heat when in use so that the housing is heated to an elevated temperature sufficient to cause a skin burn when touched by a human, a reflector arranged in the lamp housing surrounding a portion of the lamp, and a light transmissive plate arrangement closing the opening, the lamp housing and the plate defining an enclosure for an interior of the light which is free of openings, the lamp housing being made of a material having a thermal conductivity which is lower than that of human skin so that a user of the light can touch the lamp housing without adverse effects due to the elevated housing temperature and a contamination of the housing interior is prevented, wherein the lamp housing has a covering hood pivotable in an upward direction and covering sides of the reflector other than a side facing the opening, the covering hood being sufficiently pivotable so the lamp becomes accessible and can be manually exchanged.

5. Light in accordance with claim 4, including a manually actuated lock mechanism for releasably retaining the covering hood in a closed position.

6. Light in accordance with claim 5, including a spring incrementally moving the covering hood in an opening direction upon unlocking the lock mechanism such that the covering hood subsequently can comfortably be grasped and opened further.

7. Light for medical use comprising a lamp housing free of vent apertures communicating an interior of the housing with an exterior thereof, having an opening and at least one heat emitting lamp arranged in the housing interior, directing its light through the opening and generating sufficient heat when in use so that the housing is heated to an elevated temperature sufficient to cause a skin burn when touched by a human, a reflector arranged in the lamp housing surrounding a portion of the lamp, a counter-reflector which is small in relation to the reflector and arranged in front of the lamp relative to the opening, and including means for moving the counter-reflector towards and away from the reflector, and a light transmissive plate arrangement closing the opening, the lamp housing and the plate defining an enclosure for an interior of the light which is free of openings, the lamp housing being made of a material having a thermal conductivity which is lower than that of human skin so that a user of the light can touch the lamp housing without adverse effects due to the elevated housing temperature and a contamination of the housing interior is prevented.

8. Light in accordance with claim 7, including means for releasably mounting the lamp to the reflector on a side thereof facing away from the opening.

9. Light in accordance with claim 9, including a carrier rod adjustably mounting the lamp so that its position is changeable in a direction towards and away from the opening.

* * * * *